United States Patent [19]

Demmin et al.

[11] 4,335,010

[45] Jun. 15, 1982

[54] PREPARATION OF MUCONIC ACID MONONITRILES AND COPPER(II)-AMMONIA REAGENT THEREFOR

[75] Inventors: Timothy R. Demmin, Randolph; Milorad M. Rogic, Whippany, both of N.J.

[73] Assignee: Allied Corporation, Morristown, N.J.

[21] Appl. No.: 230,761

[22] Filed: Feb. 2, 1981

Related U.S. Application Data

[60] Division of Ser. No. 74,442, Sep. 11, 1979, Pat. No. 4,277,419, which is a continuation-in-part of Ser. No. 942,507, Sep. 15, 1978, abandoned.

[51] Int. Cl.$^3$ .................... C01G 3/14; C07C 120/00
[52] U.S. Cl. .......................... 252/189; 260/239.3 R; 260/438.1; 260/465.4; 423/352; 423/371
[58] Field of Search ................ 252/189; 260/239.3 R, 260/438.1, 465.4, 465 D; 423/352, 371

[56] References Cited

U.S. PATENT DOCUMENTS 4,096,190 6/1978 Rutledge .......................... 568/730
4,130,504 12/1978 Rutledge .......................... 252/430

OTHER PUBLICATIONS

H. Finkbeiner et al., J. Org. Chem., vol. 31, pp. 549–555, (1966).
I. Bodek et al., Inorganica Chimica Acta, vol. 27, pp. 213–217, (1978).
G. Davies et al., "Homogeneous Oxidative Coupling Catalysts" (unpublished manuscript).
J. Tsuji et al., Tetrahedron Letters, 1978, pp. 641–644.

Primary Examiner—Irwin Gluck
Attorney, Agent, or Firm—Alan M. Doernberg; Gerhard H. Fuchs

[57] ABSTRACT

Substituted and unsubstituted phenols, catechols and orthobenzoquinones are converted to muconic acid mononitriles by reaction with copper(II)-ammonia reagents. The copper(II)-ammonia reagents can be prepared by the reaction of cuprous chloride with oxygen or air in liquid ammonia or in ammonium hydroxide or in pyridine followed by addition of ammonia or ammonium hydroxide. The muconic acid mononitriles are useful as monomers or comonomers and as intermediates in the manufacture of substituted and unsubstituted 6-aminocaproic acids, caprolactams and polyamides.

13 Claims, No Drawings

PREPARATION OF MUCONIC ACID MONONITRILES AND COPPER(II)-AMMONIA REAGENT THEREFOR

This application is division of U.S. Ser. No. 074,442, now U.S. Pat. No. 4,277,419 which is a continuation-in-part of U.S. Ser. No. 942,507, filed Sept. 15, 1978, now abandoned.

DESCRIPTION

BACKGROUND OF THE INVENTION

Caprolactam is a widely used intermediate in the production of nylon-6 fibers, molding compounds and various plastic articles. Caprolactam is conventionally prepared by the reduction of phenol to cyclohexanone, oximation of cyclohexanone to cyclohexanone oxime and Beckmann rearrangement of cyclohexanone oxime to caprolactam. This method proceeds with high yields in all steps but employs hydroxylamine salts in various forms as the nitrogen source. Since preparation of a hydroxylamine salt solution from ammonia and other inorganic reagents can be difficult and expensive and can cause a large quantity of by-products, a need exists for a method of producing caprolactam and related amino acids without the use of hydroxylamine salts as intermediates.

The oxidative cleavage of phenol is known. Phenol can be oxidized successively to catechol (1,2-dihydroxybenzene), 1,2-benzoquinone and muconic acid monoesters. It has been reported that 4-tertbutyl-1,2-benzoquinone can be oxidized to a mixture of 3- and 4-tert-butylmuconic acid monomethyl esters by a copper(II) complex, pyridine cupric methoxy chloride in pyridine containing water. It has also been reported that phenol can be cleaved to cis,cis-muconic acid monomethyl ester in a system of pyridine cupric methoxy chloride complex and molecular oxygen.

It is also known that phenol, catechol and orthobenzoquinone can be oxidized with peracetic acid to cis,cis-muconic acid, which isomerizes, under certain conditions, to the cis,trans and trans,trans forms. The hydrogenation of muconic acid to adipic acid has also been reported. Adipic acid is commercially reacted with ammonia to form the corresponding diamide which is dehydrated and hydrogenated to hexamethylene diamine, the comonomer with adipic acid in nylon-66.

Copper-based materials are also known to catalyze the oxidative coupling of certain substituted phenols to diphenoquinones and biphenols as described, for example, in U.S. Pat. No. 4,096,190 to Rutledge (June 20, 1978). In certain examples of that patent, a copper salt and ammonia were suspended with stirring in water, a substituted phenol such as 2,6 xylenol (2,6-dimethyl phenol) was added and then oxygen flow was initiated. In example 12, the initial copper salt was cuprous chloride. It is not clear if, under such conditions, a copper(II)-ammonia reagent of the type described herein would be formed.

BRIEF DESCRIPTION OF THE INVENTION

It has been surprisingly found that phenol or catechol can be oxidatively cleaved in the presence of copper(II)-ammonia reagents to yield cis,cis-muconic acid mononitrile. The product can be hydrogenated to the commercially important 6-aminocaproic acid and caprolactam. Thus 6-aminocaproic acid and caprolactam can be made in a two-step process using easily available reagents and mild reaction conditions.

The present invention also included in its broader forms a process of preparing muconic acid mononitriles by reacting in the liquid phase a cyclic starting material selected from the group consisting of phenols of the formula

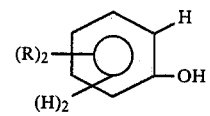

catechols of the formula

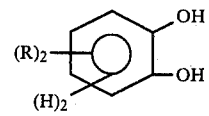

and orthobenzoquinones of the formula

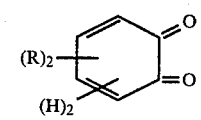

where R is independently at each occurrence H, alkyl, alkoxy, bromo, chloro, amino, phenyl, or phenoxy, with a copper(II)-ammonia reagent under reaction conditions forming a muconic acid mononitrile or a copper-(II) salt of said muconic acid mononitrile. The product may then be hydrogenated to the corresponding 6-aminocaproic acid or caprolactam.

The present invention also includes cis,cis-muconic acid mononitrile of its copper(II) salts each preferably being substantially free at the corresponding cis,trans and trans,trans as a novel composition of matter.

The present invention also includes as novel compositions the copper(II)-ammonia reagents active in the above process. This reagent is characterized by the empirical formula, when isolated, of $(CuO)(CuX_2)_y(NH_3)_z$ where X is a monovalent anion, y is between about 0.2 and about 1 and z is between about 2 and about 4. The active reagent may also be characterized as the product of the oxidation of a soluble copper(I) salt with oxygen and the reaction of the product of oxidation with ammonia. Preferably, an organic compound having a nitrogen with an unshared electron pair is present during the reaction, suitably as solvent.

DETAILED DESCRIPTION OF THE INVENTION

The oxidative cleavage of phenol and catechol with copper(II)-ammonia reagents proceeds under the mild conditions described herein to yield cis,cis-muconic acid mononitrile. Substituted phenols and catechols as described herein and unsubstituted and substituted orthobenzoquinones are expected to yield the corresponding muconic acid mononitrile under similar conditions, although the isomeric content of substituted muconic acid mononitriles is not generally expected to be as cleanly or even predominantly the cis,cis-isomer. Based upon the experiments performed, it would be expected that most mono- and di-substituted phenols, catechols and orthobenzoquinones with the substituents discussed herein would yield at least some substituted muconic acid mononitrile under similar mild conditions.

The copper(II)-ammonia reagent used herein is active to cleave phenol to cis,cis-muconic acid mononitrile in the presence of oxygen or air and to convert catechol (and presumably also orthobenzoquinone) to the same cis,cis-muconic acid mononitrile with or without air or oxygen being present. This material can be easily distingished from the cis,trans or trans,trans isomer disclosed by George Vogel in *J. Org. Chem.* 30(1), pp. 203–207 (January 1965) in having a different melting point (136°–138° C. for the cis,cis isomer compared to 110°–111° C. for the cis,trans isomer and 175°–177° C. for the trans,trans isomer in the reference) and in not showing a trans-olefin band at 970 mm in the infrared and by other spectroscopic and analytical techniques.

When the phenol, catechol or benzoquinone is substituted, the product substituted muconic acid mononitrile frequently includes at least some isomer with a trans substituted double bond. Positional isomers may also be found, based upon which of the cleavage carbons becomes a carboxylic group and which becomes a nitrile, although certain substituents may favor one or the other positional isomer. The identity of the reactant and the manner of preparing the copper(II)-ammonia reagent may affect the product isomers formed.

The muconic acid mononitriles are themselves useful as monomers or comonomers for polymeric materials. More importantly, the muconic acid mononitriles can be easily hydrogenated with Raney nickel, palladium, rhodium or other conventional hydrogenation catalysts to the corresponding 6-aminocaproic acids as follows:

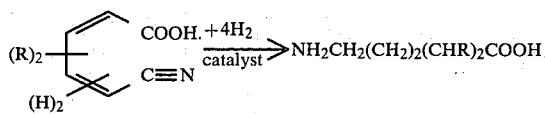

In the case of the unsubstituted cis,cis-muconic acid mononitrile itself, the product, 6-aminocaproic acid, $NH_2-(CH_2)_5COOH$ can be cyclized to caprolactam, and the caprolactam or 6-aminocaproic acid, polymerized to nylon-6.

The cyclization of 6-aminocaproic acid can be accomplished by known techniques such as heating in an alcohol as described in U.S. Pat. No. 3,988,319 to F. Mares (issued Oct. 26, 1976). It is also possible to combine the hydrogenation and cyclization as by hydrogenating in ethanol with Raney nickel or other hydrogenation catalyst and then heating to 170°–200° C. to convert the dissolved 6-aminocaproic acid to caprolactam.

The muconic acid mononitriles can also be converted to substituted 6-aminocaproic acids by addition across the double bonds. For example, chloride or bromide can be introduced onto the carbon chain by addition of $Cl_2$ or $Br_2$ and then hydrogenation to form a halogenated 6-aminocaproic acid: $NH_2-CH_2-(CXH)_4COOH$ or the like, where X is Cl or Br. It will be appreciated that the halogenated 6-aminocaproic acid can be used as a comonomer to introduce flame retardancy into polyamides.

The starting material of the present process may be a phenol, catechol or orthobenzoquinone. It is believed that during the reaction, phenols are oxidized at least to the catechol as evidenced by the requirement of oxygen in the examples wherein phenol is used. The phenols used are of the formula

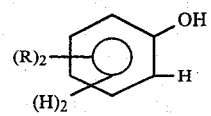

Hydrogen is required to be in at least one position adjacent to the hydroxy. 2,6-Disubstituted phenols which are incapable of being oxidized to catechols will not be cleaved by the present process, but will be polymerized or coupled (to biphenols for example) in the presence of copper(II) as is known in the art. As described in U.S. Pat. No. 4,096,190, phenols substituted on four ring positions, even if only one is adjacent to the hydroxyl, also are coupled to biphenols.

In the present invention, the starting material may also be a catechol of the formula

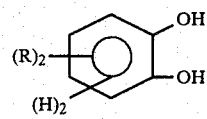

or a benzoquinone of the formula

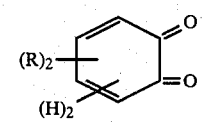

although many benzoquinones (such as when R is H in both occurrences) are less preferred as the starting material because they are less stable than the corresponding catechol or phenol.

In any of the above formulae, R may be H, alkyl, alkoxy, bromo, chloro, amino, phenyl or phenoxy. Any of the alkyl or alkoxy radicals may be straight or branched. In some starting materials, not all of these R substitutents will be inert to other reactions, nor are the listed substituents intended to be exhaustive. Thus, in some reactions, R as Br or Cl may be subjected to substitution by $NH_2$ and, if still cleaved to the muconic acid mononitrile, considered suitable, but if not so cleaved, then considered unsuitable. If reactions such as coupling of amino substituents as R to azo linkages occurs for a particular reaction, then the amino can be protected by using it in a protected form such as acetamido and then, after cleavage, converted to free amino in a conventional fashion.

The copper(II)-ammonia reagents of the present invention may be prepared in several manners. First cuprous chloride may be oxidized by $O_2$ or air or other oxidizing agent in the presence of at least about equimolar amounts of ammonia or ammonium hydroxide. The reaction may occur in ammonia, in ammonium hydroxide or in an inert organic solvent such as one containing a nitrogen with an unshared electron pair such as pyridine, dimethyl formamide or N-methylpyrrolidone. Other such appropriate solvents may include diamines such as tetramethylethylenediamine and trialkylamines such as triethylamine. While the initial oxidation may occur in ammonium hydroxide, for example, it appears necessary that an organic compound having a nitrogen with an unshared electron pair must be added at some point to activate the material. Preferably such a material is present initially, especially as the solvent. In ammonium hydroxide the reaction may be seen to occur by the appearance of a blue color which is characteristic of copper(II). Different color changes characteristic of copper(II) formation occur in pyridine: bright yellow to black-brown on oxidation, then black-brown to black-green on ammonia addition. While the ratios of cuprous chloride to oxidizing agent to ammonia or ammonium hydroxide are not critical, the oxidizing agent is preferably present in at least stoichiometric amounts compared to copper(I) (a 1:4 mole ratio in the case of $O_2$). Ammonia or ammonium hydroxide is preferably present in at least about a 1:1 mole ratio to copper preferably at least about 2:1, with excesses and even large excesses of ammonia or ammonium hydroxide being also preferred. The temperature of the oxidation of cuprous chloride is not critical, and it may be conveniently performed at $-60°$ to $+50°$ C., depending upon the solvent used. The preferred temperature for oxidation of copper(I) in liquid ammonia is $-60°$ to $-50°$ C. The preferred temperature for oxidation of copper(I) in pyridine or ammonium hydroxide is room temperature (such as 15°–30° C.).

The copper(II)-ammonia compositions or reagents of the present invention may also be prepared by oxidizing copper metal in pyridine or ammonium hydroxide to a copper(II) oxide which is inactive by Electron Spin Resonance Spectroscopy and is believed to possess paired spins and resemble the dimer formula:

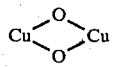

and reacting the copper(II) oxide with at least about equimolar amounts of ammonium hydroxide or ammonia, i.e. at least about a 1:1 $NH_3$:Cu molar ratio. The oxidation of copper metal is conducted in the presence of at least catalytic amounts of a copper salt such as cuprous chloride or cupric chloride causing the following proposed sequence in the case of chloride salts:

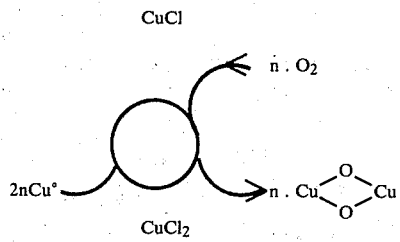

Since the copper chlorides are not consumed, pure copper metal can be continually added, producing a mixture low in copper chlorides.

The oxidation of copper metal or of cuprous chloride may be conducted in pyridine (or similar solvent) or ammonia or ammonium hydroxide. If either oxidation is conducted in pyridine, ammonia or ammonium hydroxide can either be present during oxidation, or preferably, added after oxidation.

The copper(II)-ammonia compositions or reagents of the present invention may also be prepared by reacting pyridine cupric methoxy chloride complex, a known material described by Hays et al. in *J. Am. Chem. Soc.*, vol. 81, p. 6335 (1959), with ammonia or ammonium hydroxide. In the presence of water alone the pyridine cupric methoxy chloride in pyridine is active to form muconic acid monomethyl ester as described in our Communication in *J. Am. Chem. Soc.*, vol. 98, pp. 7441–7443 (1976). Free methanol may be removed from the copper(II)-ammonia reagent, as by evaporation, so that the reagent can, in some cases, produce more mononitrile and less monoester when reacted with the cyclic starting material.

In the foregoing discussion, copper(I) chloride is described as the CuX starting material. Salts of copper(I) and other monovalent anions such as I, Br, acetate and benzoate may also be used, however, to prepare copper(II)-ammonia reagents which are also active to convert cycling starting materials to muconic acid mononitriles, but not necessarily to the same degree. Thus, for example, reagents formed from CuBr are generally comparable in activity to those formed from CuCl, while reagents formed from CuI appear somewhat less active. Other soluble copper(I) salts such as copper(I) acetate and copper(I) benzoate may also be used by oxidizing them with oxygen and adding ammonia or ammonium hydroxide to the product.

The copper(II)-ammonia reagents of the present invention are useful not only to cleave phenols, catechols and orthobenzoquinones to muconic acid mononitriles, but also to convert various aldehydes to nitriles. It is possible that the conversion of an aldehyde to a nitrile may form a part of the mechanism of the overall phenol cleavage reaction.

The present invention is thus contemplated to include active copper(II)-ammonia reagents prepared by each of the above techniques which are believed to represent novel methods as well. It is not asserted that the identical reagent is prepared by each of the above techniques, and in fact there is some evidence that different methods produce different but analogous reagents which cause different product mixtures in some cleavage reactions.

In general, the active copper(II)-ammonia reagent can be characterized by the empirical formula, when recovered from a solvent, of $(CuO)(CuX_2)_y(NH_3)_z$ where x is a monovalent anion such as Cl, Br, I, acetate or benzoate; y is between about 0.2 and about 1 and z is between about 2 and 4.

Unless extraordinary measures are taken during preparation to enhance the CuO component relative to the $CuX_2$ component, they will generally be about equimolar such that the empirical formula becomes $Cu_2OX_2(NH_3)_z$. When z is less than 4 (or less than two times the moles of copper in the more general formula), the difference is normally made up by ligands of the organic nitrogen-containing solvent.

Representative copper(II)-ammonia reagents thus have the following empirical formulae:
$Cu_2OCl_2(NH_3)_4$
$Cu_2OBr_2(NH_3)_4$
$Cu_2OCl_2(NH_3)_3(py)$
$Cu_2OCl_2(NH_3)_3$ (DMF)
$Cu_2OBr_2(NH_3)_3(py)$
$Cu_{1.5}OBr(NH_3)_3$
$Cu_2OI_2(NH_3)_4$
$Cu_2O(CH_3COO)_2(NH_3)_4$ It should be appreciated that the active reagent itself need not be soluble in the solvent employed, but may instead be suspended (preferably in very small particles) in the solvent. Thus, for example, when CuCl is oxidized, the resulting mixture of copper(II) oxide and copper(II) chloride is soluble in, for example, pyridine. When ammonia is added, however, the active reagent precipitates in fine particles forming a suspension that is active for the conversion of a catechol to a muconic acid mononitrile. As shown by the examples, this suspension can be separated from the solvent, and an aliquot characterized as to empirical formula, and then the precipitate resuspended in an appropriate solvent and used to convert a catechol to a muconic acid mononitrile.

In the reaction mixture which includes the cyclic starting material, copper is preferably less than about 0.5 molar (regardless of solvent) because more concentrated copper can cause polymerization. More preferred is about 0.05 to about 0.2 molar copper.

The copper(II)-ammonia reagent is preferably present in at least about stoichiometric amounts compared to the cyclic starting material. In theory, the cleavage of quinones is a two electron oxidation, the cleavage of catechols is a four electron oxidation and the cleavage of phenols is a six electron oxidation. Accordingly, molar ratios of copper(II) starting material of 2:1, 4:1 and 6:1 might appear necessary for quinones, catechols and phenols respectively. Under aerobic conditions, however, oxygen may oxidize cyclic starting material or reduced forms of copper formed during the reaction. Accordingly, lower molar ratios (especially lower than 6:1 for phenols) may be in excess of stoichiometric amounts under actual conditions. At present, molar ratios of at least 2:1 are preferred for all starting materials.

When less than a 2:1 molar ratio of copper(II) ammonia reagent to starting material is used, a lesser amount of the starting material would be converted to product unless inorganic copper salts are recovered from the product and converted back to the copper(II)-ammonia reagent.

The preferred temperature range for the cleavage reaction is between about 15° C. and about 35° C., with a suitable overall range being about 0° C. to about 50° C. Temperatures much below room temperature are less preferred for phenols because the reaction is slowed down. Temperatures much above room temperature are somewhat less preferred for all starting materials because of a possible increase in polymerization rates of the reagent or the organic materials and thus lowered yields. While the reaction may be performed at atmospheric pressure or below, superatmospheric pressures can cause increased reaction rates, especially for phenols.

The reaction mixture after the oxidative cleavage reaction contains copper salts of muconic acid mononitriles which, if oxygen is added during reaction, appear to be copper(II) salts and, if oxygen is not present during reaction, appear to be mixtures of copper(I) salts and copper(II) salts. The reaction mixture also usually contains other copper-containing materials including, perhaps, a form of copper(II) chloride in the reaction mixture when copper(I) chloride is the original copper source and oxygen is present in excess during the reaction. The copper salt or salts of muconic acid mononitrile can be concentrated by filtering out the suspended copper salts and evaporating off the solvent. If one desires to purify the copper(II) salts further, one would then purify the residue by conventional techniques such as recrystallization from a suitable solvent which could be dimethyl formamide, acetonitrile, pyridine or a suitable combination of these solvents, or by a suitable chromatography technique.

To recover the muconic acid mononitrile itself, the crude copper salts of muconic acid mononitrile are hydrolyzed with an inorganic acid; and the muconic acid mononitrile is extracted into an organic layer. In some of the following examples these steps are combined by adding HCl in ether. Filtration after acidification and addition of the organic solvent produces solid salts (which appear to be copper(II) chloride when copper(I) chloride is the copper source, oxygen is added during reaction and HCl is the acid used for hydrolysis) and a filtrate of the muconic acid mononitrile in the organic solvent. The mononitrile can be recovered from the filtrate by evaporating off the solvent. If care is taken to exclude oxygen from this workup, the valence of the solid copper salts filtered out in the last step should be indicative of the valence of copper in the copper salts of muconic acid mononitrile originally formed. Based upon the appearance of the solid copper salts recovered from most work-ups, it appears that the original copper salts are copper(II) salts in the presence of excess oxygen but can be caused to include at least a portion of copper(I) salts if the oxygen present during the reaction is limited.

As illustrated by the Examples that follow, the initial product mononitrile is in the cis,cis-configuration when unsubstituted, but can contain other isomers even in major proportions under certain conditions when substituted as by a tertiary butyl group. If it is desired to separate these isomers, this can be accomplished by conventional chromatographic techniques. If it is desired to produce cis,trans or trans,trans isomers from an initial cis,cis isomer, this ought to be accomplished by conventional techniques such as heating the nitrile in the molten state or subjecting the nitrile in solution to an appropriate isomerizing radiation. Such isomerization of muconic acid itself is described in an article entitled, "The Third Isomeric (cis-trans-) Muconic Acid" by J. A. Elvidge et al. at *J. Chem. Soc.* pp. 2235-41 (1950). This article demonstrates that cis,cis-muconic acid is readily inverted to cis,trans-muconic acid (as by crystallization from boiling water) and that both the cis,cis and cis,trans isomers can be isomerized to the trans,trans isomer by irradiation by ultraviolet light in water containing a trace of iodine. No evidence is presented that the reverse inversions of muconic acid (trans,trans to either other form or cis,trans to cis,cis) takes place.

EXAMPLE 1

Phenol as Reactant—Ammonia

Cuprous chloride (60 grams, 600 millimoles) in about 300 milliliters of liquid ammonia at −55° C. was oxidized with molecular oxygen for 2–3 hours to give a dark heterogeneous mixture. Dry pyridine (3000 mL) was added and, under nitrogen, the mixture was warmed to 0° C. with loss of excess ammonia. Oxygen and ammonia were bubbled through the vigorously stirred mixture and phenol (14.1 grams, 150 millimoles) in about 30 mL of pyridine was added. The mixture was warmed to room temperature and maintained there for a total of 16 hours with stirring and continued ammonia and oxygen introduction. The mixture was then evaporated under vacuum at 25°–30° C. and the solid residue extracted with 600 mL of diethyl ether followed by filtration. Evaporation of ether from the liquid gave 8.4 grams of phenol with a trace of green copper salts and pyridine. The green-black solid filtrate was suspended in 600 mL of ether and cooled to 0° C. with stirring. HCl was added in the form of 125 mL of ether saturated with HCl over 15 minutes, with constant stirring, followed by 30 minutes of additional stirring at 0° C. The yellow solid (apparently inpure copper(II) chloride) was then filtered out and the filtrate (dark red solution) dried and evaporated to 5.3 grams of a brown solid. Analysis of the brown solid by nmr indicated about half cis,cis-muconic acid mononitrile and about half phenol, representing a 24% conversion and a 60% yield.

EXAMPLE 2

Example 1 was repeated with 50 millimoles of phenol. 200 millimoles of CuCl in liquid ammonia were oxidized at −60° C. and dissolved in 1000 mL pyridine. After phenol addition, the reaction occurred over 18.5 hours at room temperature with only oxygen (not ammonia) being added. The product was hydrolyzed at 0° C. with 200 mL concentrated HCl in 1200 mL methylene chloride. The conversion of phenol was about 74%, the yield about 39%. The lower yield is believed due to product solubility and further reaction of the product in or with aqueous acid. Small amounts of muconic acid monophenyl ester and 3-phenoxy muconic acid monophenyl ester were observed as by-products by nmr.

EXAMPLE 3

Example 2 was repeated except that oxygen and ammonia were added during the 18 hour reaction period and the product mixture stored for 48 hours under nitrogen before extraction and hydrolysis with concentrated HCl in methylene chloride. The conversion was about 71%, the yield of mononitrile about 57% and the same trace by-products detected by nmr.

EXAMPLE 4

Phenol as Reactant—Ammonium Hydroxide 20 millimoles of CuCl in 100 mL of concentrated ammonium hydroxide at room temperature were oxidized with molecular oxygen for 2–3 hours. 10 millimoles of phenol in 7 mL of concentrated ammonium hydroxide were added and the reaction conducted at room temperature over 18.5 hours with oxygen added by continuous bubbling at 1 atmosphere. The product was hydrolyzed with 125 mL concentrated HCl in 500 mL CH$_2$Cl$_2$ giving a 77% conversion of phenol and a 23% yield of mononitrile. No phenyl ester products were detected by nmr.

EXAMPLE 5

4-Tert-Butyl-Phenol as Reactant—Ammonia

Example 2 was repeated with 50 millimoles of phenol added to the reactant formed from 200 millimoles CuCl and ammonia at −60° C. which had been dissolved in 1 liter of pyridine. The reaction, at room temperature over 18 hours with oxygen and ammonia being added, resulted in a 65% conversion of phenol and a 19% yield of material tentatively identified as

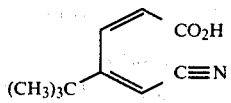

as the only muconic acid mononitrile isomer.

EXAMPLE 6

4-Tert-Butyl-Catechol-Copper Methoxy Chloride-Ammonia

Pyridine (80 mL) was saturated with anhydrous ammonia for 15 minutes at room temperature and then cooled to 0° under nitrogen. Pyridine copper methoxy chloride (8.4 g, 40 mmol) was added and the mixture was again warmed to room temperature. A solution of 4-tert-butylcatechol (0.83 g, 5 mmol) in 5 mL of pyridine was added over 15 minutes via pump driven syringe. After stirring an additional 40 minutes the mixture was evaporated to dryness, extracted with 500 mL of pentane, and the filtered solid was hydrolyzed in a stirred mixture of methylene chloride (500 mL) and 6 N aqueous HCl at 0° for 45 minutes. The organic layer was dried and evaporated to give 0.96 g of brown oil. Dissolving in methylene chloride and extraction with saturated NaHCO$_3$ solution gave a neutral fraction, 0.40 g, of reddish solid A and an acid fraction, 0.45 g, of light yellow oil B. A was identified as 4-tert-butyloxacyclohepta-3,5-dien-2,7-dione by ir, pmr, cmr, ms and elemental analysis. B was identified by ir, pmr, cmr, ms and elemental analysis as a mixture of three isomers of B-tert-butylmuconic acid mononitrile. These were tentatively identified as 4-tert-butyl-cis,cis-2,4-hexadiendioic acid C$_6$-mononitrile; 3-tert-butyl-cis, trans-2,4-hexadiendioic acid C$_6$-mononitrile and 3-tert-butyl-cis,cis-2,4-hexadiendioic acid C$_6$-mononitrile.

EXAMPLE 7

Example 6 was repeated using 4-tert-butyl-o-benzoquinone and gave the same product mixture under similar conditions.

EXAMPLE 8

Example 6 was repeated using catechol to produce cis,cis-muconic acid mononitrile (40% yield) and a trace of cis,cis-muconic acid monomethyl ester under similar conditions.

EXAMPLE 9

4-tert-butyl-catechol—Ammonium Hydroxide

Following the general procedure of Example 1, a reagent was prepared by oxidizing 300 millimoles of CuCl with molecular oxygen in 600 mL pyridine followed by the addition of 15 mL of concentration ammonium hydroxide. 25 millimoles of 4-tert-butylcatechol were added over 30 minutes with vigorous stirring and the reaction given 15 additional minutes, all at room temperature. Essentially complete conversion of catechol resulted in about 50% yield of

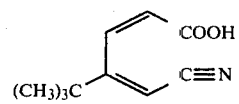

as the main isomer. Small amounts of two other isomers and unidentified by-products were also detected by nmr this structure of the main product was confirmed by a combination of nmr, cmr, ir, uv, mass spectroscopy and elemental analysis.

EXAMPLE 10

A solution of cuprous chloride (5.93 g, 60 mmol) in pyridine (120 mL) was oxidized with molecular oxygen at room temperature. With cooling in an ice bath, the solution was saturated with anhydrous ammonia. A solution of catechol (0.55 g, 5 mmol) in pyridine (10 mL) was added over 25 minutes to the stirred mixture under an oxygen atmosphere. After stirring for an additional 15 minutes, the product was evaporated to dryness in vacuo at +25 − +30° C. and then redissolved in 400 mL of methylene chloride and hydrolyzed at 0° with 200 mL of 6 N HCl for 45 min. The bright green acid layer, containing copper(II) salts, was separated from the organic layer. The organic layer was dried and evaporated to give about 0.16 g (26% yield) of solid, shown by nmr and ir to be cis,cis-muconic acid mononitrile, mp 133°–135° C.

EXAMPLE 11

Example 10 was repeated with concentrated ammonium hydroxide as solvent for oxidation, with the same product in approximately same yield.

EXAMPLE 12

High Pressure Cleavage Reaction 20 millimoles of CuCl dissolved in 100 mL of pyridine were oxidized with molecular oxygen for one hour at room temperature. Then anhydrous ammonia gas was bubbled through the mixture for 15 minutes to form the copper(II)-ammonia reagent and phenol (0.94 g, 10 millimoles) added to form the reaction mixture. The reaction mixture was then pressurized with molecular oxygen to 60 psi gage (about 515 kPa absolute pressure) and stirred for 1–2 hours at room temperature. The crude product was then worked up with concentrated hydrochloric acid in methylene chloride at 0° C. and cis,cis-muconic acid mononitrile identified in the product along with unreacted phenol. The conversion was 65% and the yield was 24%.

Examples 1–12 are summarized in the following Table 1 wherein 4TBP=4-tert-butylphenol, 4TBC=4-tert-butylcatechol, 4TBQ=4-tert-butyl-o-benzoquinone and PyCuOMeCl is the complex pyridine cupric methoxy chloride.

The nitrogen source to convert the copper material to the active reagent was ammonia in Examples 1–3, 5–8 and 10–12 and ammonium hydroxide in Examples 4 and 9.

The solvent for cleavage was pyridine in Examples 1–3, 5–10 and 12 and ammonium hydroxide in Examples 4 and 11.

Gas addition during reaction was oxygen alone in Examples 2 and 4, oxygen and ammonia in Examples 1, 3, 5 and 12, oxygen-containing atmosphere in Examples 10 and 11 and none in Examples 6–9.

Work-up of the product was with ether-HCl in Example 1, concentrated HCl in methylene chloride in Examples 2–4 and 6 N aqueous HCl in methylene chloride in Examples 5–12.

TABLE I

| Ex | SM | Cu | Conversion | Yield | Comments |
|----|------|------|------|------|------|
| 1 | Phenol | CuCl | 24% | 60% | |
| 2 | Phenol | CuCl | 74 | 39 | small amounts phenyl esters |
| 3 | Phenol | CuCl | 71 | 57 | trace of phenyl esters |
| 4 | Phenol | CuCl | 77 | 23 | no phenyl esters |
| 5 | 4TBP | CuCl | 65 | 19 | only one isomer |
| 6 | 4TBC | PyCuOMeCl | complete | | 3 isomers + "cyclic" |
| 7 | 4TBQ | PyCuOMeCl | complete | | 3 isomers + "cyclic" |
| 8 | Catechol | PyCuOMeCl | complete | about 40 | trace of mono-methyl ester |
| 9 | 4TBC | CuCl | complete | about 50 | one main product, small amounts other isomer and by-products |
| 10 | Catechol | CuCl | complete | 26% | |
| 11 | Catechol | CuCl | complete | about 25% | |
| 12 | Phenol | CuCl | 65% | 24% | Cleavage at 60 psig pressure of oxygen |

EXAMPLE 13

Hydrogenation With Raney Nickel

Cis,cis-muconic acid mononitrile (0.5 grams) prepared as in Example 1 was dissolved in 250 mL of dry ethanol saturated with ammonia. Excess Raney Nickel was added and the stirred solution treated with $H_2$ (at 1000 psi gage or about 7 MPa absolute pressure) for 15 hours at room temperature. Excess catalyst was removed by filtration and the solution evaporated to dryness. Remaining catalyst was removed by adding about 5 mL water and filtering. Evaporating the aqueous layer gave about 0.5 grams of an off white solid identified by infrared and n m r as 6-aminocaproic acid.

Based upon the known process of Mares, it would be expected that heating the 6-aminocaproic acid in ethanol before isolation to about 170°–200° C. would result in cyclization. It would also be expected that the crude product of cleavage before hydrolysis (probably the copper salt of muconic acid mononitrile) could be directly hydrogenated to 6-aminocaproic acid.

EXAMPLE 14

Hydrogenation With Rhodium

When example 13 is repeated using glacial acetic acid as solvent and 5% rhodium on carbon as catalyst, 6-aminocaproic acid was obtained in similar yield, but with easier separation of product and catalyst.

Physical Data

The following data for cis,cis-muconic acid mononitrile (cis-5-cyano-cis-2,4-pentadienoic acid) was obtained from the products of several different Examples (1–4, 8 and 10–12). In each above Example, ir and nmr spectra were performed to analyze for the product. The other physical data were obtained only on some specimens.

Melting point—136°–138° C. 30,

Ultraviolet: $\lambda_{max}CH_3CN$ 259 nm ($\epsilon15,900$), 290 nm (sh), $\lambda_{max}MeOH$ 257 nm ($\epsilon16,100$).

Infrared (NUJOL): 3350–2230 (CO$_2$H), 2215 (—CN), 1775 (CO$_2$H), 1675 (shoulder), 1621, 1564, 1452, 1347, 1305, 1262, 1198, 921, 840, 782, 693 and 667.

NMR ((CD$_3$)$_2$CO): δ5.78 (d of t, 11 and <1 Hz, =CH—CO$_2$—, 1), 6.12 (d of t, 11 and <1 Hz, =CH—CN, 1), 7.00 (t of d, 11 and <1 Hz, —CH=C—CN, 1), 8.13 (t of d, 11 and <1 Hz, —CH=C—CO$_2$—, 1) and 9.85 (bs, CO$_2$H, 1).

These tentative assignments are internally consistent based on decoupling experiments.

CMR (CDCl$_3$) δ105.47 (=CH—CN), 115.09 (—CN), 124.83 (=CH—CO$_2$—), 139.11 (—CH=C—CN), 142.97 (—CH=C—CO$_2$) and 169.81 (—CO$_2$H).

ANAL C$_6$H$_5$NO$_2$; Calc: C 58.53, H 4.09, N 11.38, Found: C 58.83, H 4.18, N 11.17.

Mass Spec (C.I./NH$_3$): 124 for molecule plus a proton (thus molecular weight is 123).

EXAMPLE 15

Copper(II)-Ammonia Reagent from CuCl

A solution of CuCl (10.0 g, 0.101 moles) in 500 mL of dry pyridine has oxidized at room temperature with molecular oxygen for about 1 hour until no further uptake was observed. The solution was cooled to 0° C. and anhydrous ammonia gas was passed over the rapidly stirred mixture for 30–60 minutes. The dark heterogeneous mixture was filtered at 0° under argon through a medium porosity glass frit built into the bottom of the reactor flask. The pyridine was virtually colorless and contained very little copper salts. The dark olive green insoluble copper(II)-ammonia complex was then rinsed with dry ether (twice with 500 mL) and dried in vacuo (about 1 mm Hg) at 0° for 1 hour and at 20° C. for 30 minutes to give 14.6 g of olive green chunks which were stored at 0° under argon. Analysis of an aliquot of this material produced the following results:

Infrared (NUJOL): 3320(b,s), 3210(sh), 3160(sh), 1610(b,s), ~1260(sh), 1230(s), 740, and 695.

Analysis: Cu$_2$Cl$_2$ON$_4$H$_{12}$ Calc: C, 0.00; H, 4.29; N, 19.86; Cu, 45.04; Cl, 25.14; O, 5.67; Found: (a) C, 3.98; H, 3.90; N, 18.19; Cu, 40.79; Cl, 23.06; O, 10.03, (b) C, 4.14; H, 4.64; N, 18.51; Cu, 41.58; Cl, 22.72; O, 8.72.

Empirical formula (a) & (b) C$_{0.5}$H$_{6-7}$N$_2$Cu$_2$Cl$_2$O$_{0.8-1.0}$

X-ray Diffraction: Amorphous

The presence of carbon in the two elemental analyses has not been explained. Additionally, the technique for analyzing for oxygen is not as precise as some of the other elements such that the indicated values are approximations.

EXAMPLE 16

Oxidation of 4-tert-Butylcatechol with Copper(II)-Ammonia Reagent (from CuCl)

The isolated copper(II)-ammonia reagent (7.00 g, 50 mmole) of Example 15 was suspended in 400 mL of dry pyridine under nitrogen at 0° C. A solution of 4-tert-butylcatechol (1.66 g, 10 mmole) in 6 mL of pyridine was added via pump-driven syringe over 60 minutes with an additional 30 minutes of stirring at 0° C. The material was evaporated to dryness in vacuo at 25°–30° C., and hydrolyzed at 0° with 120 mL of 6 N HCl in the presence of 500 mL of methylene chloride. The organic layer was concentrated to 100 mL volume and extracted with 100 mL of saturated NaHCO$_3$ solution. The base layer was re-acidified at 0° C. in the presence of 100 mL of methylene chloride. The organic layer was dried and evaporated to give 0.80 g (45% yield) of β-tert-butylmuconic acid mononitrile as an oily solid mixture of three isomers identified by infrared and nmr spectra. The isomers were identified as 4-tert-butyl-cis,cis-2,4-hexadienedioic acid C$_6$-mononitrile (about 50%); 3-tert-butyl-cis,trans-2,4-hexadienedioic acid C$_6$-mononitrile (about 40%) and 3-tert-butyl-cis,cis-2,4-hexadienedioic acid C$_6$-mononitrile (about 10%).

EXAMPLE 17

N,N-Dimethylformamide as a Solvent in an Oxidation with Copper(II)-Ammonia Reagent N,N-Dimethylformamide was used in place of pyridine in a reaction similar to that of Example 16 using a copper(II)-ammonia reagent prepared as in Example 15. After stirring under nitrogen for 20 hours at 0° C., the mixture was hydrolyzed in the presence of methylene chloride. Extraction with NaHCO$_3$ solution and re-acidification provided a mixture of two isomers of β-tert-butylmuconic acid mononitrile in 25% yield by nmr spectral analysis.

EXAMPLE 18

N,N-Dimethylformamide as Solvent in the Oxidation of CuCl.

Following the procedure of Example 15 CuCl (2.00 g, 20 mmole) was partially dissolved in 200 mL of N,N-dimethylformamide. The system was mechanically stirred at room temperature under an oxygen atmosphere. After 2 hours, oxygen uptake ceased at 63.5 mL (57% of theoretical) providing a clear dark brown solution. The solution was cooled to 0° C., anhydrous ammonia was passed over the stirred mixture for 30 mins and 4-tert-butyl-catechol (0.42 g, 2.53 mmole) in 5 mL of N,N-dimethylformamide was added via pump driven syringe over 30 min. After stirring under argon for 17 hours at 0° C., the mixture was concentrated in vacuo and stirred at 0° with 250 mL of 40% aqueous HCl in the presence of 400 mL of methylene chloride. Extraction with NaHCO$_3$ solution and re-acidification provided β-tert-butylmuconic acid mononitrile in 20% yield by nmr spectral analysis.

EXAMPLE 19

N-Methylpyrrolidone as Solvent in the Oxidation of CuCl.

According to the procedure in Example 18 CuCl was partially dissolved in N-methylpyrrolidone at room temperature and stirred under oxygen overnight. Oxygen uptake stopped at 120% of theoretical. Anhydrous ammonia and then 4-tert-butylcatechol were added under argon. After stirring 18 hours at 0° C., the mixture was acidified with 100 mL of 40% aqueous HCl in the presence of 150 mL of methylene chloride. Extraction with NaHCO$_3$ solution, re-acidification, and removal of volatiles gave β-tert-butylmuconic acid mononitrile.

EXAMPLE 20

Preparation of the Copper(II)-Ammonia Reagent from CuBr

Following a procedure analogous to that of Example 15, CuBr (3.25 g, 22.7 mmole) in dry pyridine (500 mL) was stirred under oxygen at room temperature overnight at which point the theoretical amount of oxygen was consumed. The dark heterogeneous mixture was cooled to 0° C., treated with anhydrous ammonia and the insoluble copper(II)-ammonia complex was isolated, as before, yielding 4.12 g of dark olive green chunks. The solid material was analyzed as follows:

Infrared (NUJOL): 3310(b,s), 3222(sh), 3160(sh), 1606, 1267, 1240 and 702.

ANAL: $Cu_2Br_2ON_4H_{12}$ Calc: C, 0.00; H, 3.26; N, 15.10; Cu, 34.25; Br, 43.08; O, 4.31, Found: C, 1.15; H, 2.98; N, 12.35; Cu, 34.62; Br, 43.22; O, 5.88.

EXAMPLE 21

Preparation of the Copper(II)-Ammonia Reagent from CuI

Following the procedure in Example 15, CuI (2.88 g, 15.1 mmole) in dry pyridine (300 mL) was stirred under oxygen in the presence of a catalytic amount of CuCl (0.15 g, 1.5 mmole) at room temperature for three days at which point the theoretical amount of oxygen was consumed. The dark heterogeneous mixture was cooled to 0° C., treated with anhydrous ammonia and the insoluble copper(II)-ammonia complex was isolated, as before, yielding 2.72 g of green-blue chunks. The solid material, which is very unstable to oxidation of iodide by oxygen, was analyzed as follows:

Infrared (NUJOL): 3310(b,s), 3230(sh), 3150(sh), 1604, 1237, 715 and 695.

ANAL: $Cu_2I_2ON_4H_{12}$ Calc: C, 0.00; H, 2.60; N, 12.05; Cu 27.33; I, 54.58; O, 3.44, Found: C, 3.26; H, 3.22; N, 13.45; Cu 26.91; I, 43.33; O, 9.64.

EXAMPLE 22

Oxidation of 4-tert-Butylcatechol with the Copper(II)-Ammonia Reagent from CuBr

Following the procedure in Example 20, a copper(II)-ammonia complex was prepared from 3.00 g (20.9 mmole) of CuBr in 200 mL of dry pyridine. After the ammonia addition was complete, the system was stirred under argon at 0° C. as 4-tert-butylcatechol (0.83 g, 5.0 mmole) in 6 mL of pyridine was added over 45 minutes. After stirring an additional 45 minutes at 0° C. under argon, the mixture was brought to 25° C. during the evaporation and the product was isolated in the standard manner. The yield of β-tert-butylmuconic acid mononitrile was 0.34 g (38% yield) of light tan crystals composed of a mixture of isomers.

EXAMPLE 23

Oxidation of 4-tert-Butylcatechol with the Copper(II)-Ammonia Reagent From CuI

Following the procedure of Example 21, a copper(II)-ammonia complex was prepared from 3.81 g (20.0 mmole) of CuI in 200 mL of pyridine containing a catalytic quantity (0.2 g) of CuCl. After the ammonia addition was complete, the system was stirred under argon at room temperature as 4-tert-butylcatechol (0.83 g, 5.0 mmole) in 7 mL of pyridine was added over one hour. After stirring an additional one hour at room temperature, the mixture was stoppered and placed in a refrigerator for one week before the standard isolation. A single isomer, 4-tert-butyl-cis,cis-2,4-hexadiendioic acid $C_6$-mononitrile was isolated in 12% yield and identified by infrared and nmr spectral analyses.

EXAMPLE 24

Copper(II)-Ammonia Reagent from CuCl and Ammonium Hydroxide

Following the procedure of Example 15, CuCl (10.0 g, 10.1 mmoles) was oxidized in pyridine at room temperature with molecular oxygen. After cooling to 0° C., the solution was treated with concentrated ammonium hydroxide (27 mL, about 400 mmoles), stirred 20 minutes at 0° C., filtered and rinsed with diethyl ether (twice with 500 mL). The dark insoluble material was evaporated at 0° C. for 30 minutes and at 20° C. for 3 hours to give 14.49 g of the complex as light olive green chunks which were stored under nitrogen in the refrigerator.

Infrared (NUJOL): 3675, 3315, 3220, 3160, 1613, 1233 and 732.

ANALYSIS: $CuClO_{1/2}(NH_3)_2$ Calc: C, 0.00; H, 4.29; N, 19.86, Cu, 45.04; Cl, 25.14; O, 5.67. Found: C, <0.05; H, 4.34; N, 19.76; Cu, 45.05; Cl, 25.11; O, 5.66.

X-Ray Diffraction: Apparently entirely crystalline; major phase is $CuCl_2(NH_3)_2$ and minor phase could not be identified.

EXAMPLE 25

Oxidation of 4-tert-Butylcatechol with Copper(II)-Ammonia Reagent (from CuCl and Ammonia Hydroxide)

Following the procedure in Example 16, 4-tert-butylcatechol (0.83 g, 5 mmoles) was oxidized with the copper(II)-ammonia reagent from Example 24, 3.50 g. Standard workup provided 0.10 g (11% yield) of β-tert-butylmuconic acid mononitrile as oily tan crystals.

COMPARATIVE EXAMPLE 26

Attempted Preparation of Cis,Cis Muconic Acid Mononitrile From Monoesters

Cis,cis-muconic acid monomethyl ester prepared by the techniques of our Communication in J. Am. Chem. Soc. Vol. 98, pp. 7441-7443 was converted to the acid chloride by reacting with thionyl chloride under reflux conditions. Nmr analysis of an aliquot of the crude product showed a mixture of isomers. The crude mixture was then treated with excess lithium tri-tert-butoxyaluminum hydride in di-2-methoxyethyl ether at −70° C. with hydrolysis at −70° C. The predominant isomer was the cis,-trans isomer:

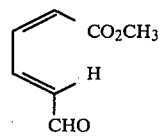

Thus, these first steps in producing a mononitrile via the oxime caused inversion. It is clear that converting the acid chloride to nitrile by the other standard route, i.e. amide formation followed by dehydration and ester hydrolysis, would also yield an isomeric mixture in which the cis,cis isomer is at most a minor component. The 1975 article by George Vogel demonstrates that cyanide addition to the corresponding 5-carbon material yields a cis,trans muconic acid monontrile isomer.

What is claimed is:

1. A method of forming a copper(II)-ammonia reagent which comprises oxidizing a soluble cuprous salt with oxygen in an organic solvent containing a nitrogen with an unshared electron pair and reacting the product with ammonia or ammonium hydroxide.

2. The method of claim 1 wherein the organic solvent is pyridine.

3. The method of claim 1 wherein ammonia or ammonium hydroxide is added after the oxidation.

4. The method of claim 1 wherein ammonia or ammonium hydroxide is present during oxidation.

5. The method of claim 1 or 2 wherein the soluble cuprous salt is cuprous chloride.

6. A copper(II)-ammonia reagent prepared by the method of claim 5.

7. A copper(II)-ammonia reagent prepared by the method of claim 1 or 2.

8. A copper(II)-ammonia reagent active for the conversion of catechols to muconic acid mononitriles being suspendable in at least one organic solvent containing a nitrogen with an unshared electron pair and having an empirical formula when isolated from such an organic solvent of $$(CuO)(CuX_2)_y(NH_3)_z$$

where X is a monovalent anion, y is between about 0.2 and about 1 and z is between about 2 and about 4.

9. The copper(II)-ammonia reagent of claim 8 wherein X is a monovalent anion selected from the group consisting of chloride, bromide and iodide.

10. The copper(II)-ammonia reagent of claim 9 wherein X is chloride.

11. The copper(II)-ammonia reagent of claim 9 where X is bromide.

12. The copper(II)-ammonia reagent of claim 8 or 9 wherein said empirical formula is $$Cu_2OX_2(NH_3)_z.$$

13. The copper(II)-ammonia reagent of claim 12 wherein z is about 4.

* * * * *